(12) United States Patent
Sen (10) Patent No.: US 8,167,851 B2
(45) Date of Patent: May 1, 2012

(54) SAFETY TRANSFUSION CATHETER (75) Inventor: Luyi Sen, Shanghai (CN)

(73) Assignee: Sun Medical-Scientific (Shanghai) Co., Ltd., Pudong New Area, Shanghai (CN)

( * ) Notice: Subject to any disclaimer, the term of this patent is extended or adjusted under 35 U.S.C. 154(b) by 330 days.

(21) Appl. No.: 12/446,755

(22) PCT Filed: Oct. 22, 2007

(86) PCT No.: PCT/CN2007/003007
§ 371 (c)(1),
(2), (4) Date: Apr. 23, 2009

(87) PCT Pub. No.: WO2008/049331
PCT Pub. Date: May 2, 2008

(65) Prior Publication Data
US 2010/0036331 A1     Feb. 11, 2010

(30) Foreign Application Priority Data

Oct. 23, 2006 (CN) .......................... 2006 1 0117448
Oct. 23, 2006 (CN) ....................... 2006 2 0047022 U
Oct. 23, 2006 (CN) ....................... 2006 2 0047024 U (51) Int. Cl.
*A61M 5/00* (2006.01)
*A61M 5/32* (2006.01)
(52) U.S. Cl. ...................................... 604/263; 604/272

(58) Field of Classification Search .................. 604/263, 604/272–274, 160
See application file for complete search history.

(56) References Cited

U.S. PATENT DOCUMENTS

| | | | | |
|---|---|---|---|---|
| 3,670,729 | A * | 6/1972 | Bennett et al. | 604/500 |
| 3,827,434 | A * | 8/1974 | Thompson et al. | 604/160 |
| 6,607,511 | B2 * | 8/2003 | Halseth et al. | 604/164.08 |

* cited by examiner

*Primary Examiner* — Jackie Ho
*Assistant Examiner* — Imani Hayman (57) ABSTRACT

A safety transfusion catheter includes a flexible retention tube fitted over a metal guiding needle. The flexible retention tube is provided with a needle handle connected with it. The angle between the end of the flexible retention tube and its longitudinal axis or longitudinal tube wall is less than 90.degree. The cross section of the needle handle has an outer contour line of a closed curve formed with a curve intersecting a beeline. A further safety transfusion catheter includes a flexible retention tube fitted over a metal guiding needle, a transfusion connecting tube in fluid communication with flexible retention tube and a rubber casing cap at the end of the flexible retention tube. The transfusion connecting tube and flexible retention tube form a T-shaped or an oblique Y-shaped structure.

14 Claims, 6 Drawing Sheets

SAFETY TRANSFUSION CATHETER

RELATED APPLICATIONS

The present application is related to Chinese Provisional Patent Application serial no. 200610117448.7, 200620047022.4, 200620047024.3, all of them filed on Oct. 23, 2006, which is incorporated herein by reference and to which priority is claimed pursuant to PCT A61M 5/158, A61M 25/06, A61M 5/31, respectively.

BACKGROUND OF THE PRESENT INVENTION

1. Field of Invention

The present invention relates to a medical device, and more particularly to a device which is adapted for infusing a liquid into the vessel of human body.

2. Description of Related Arts

Intravenous infusion (currently called infusion) remains the major procedure for clinical care and treatment, particularly, in the intensive care unit, emergency room, etc., immediately establishing the intravenous transfusion is often the key elements of life-saving.

Rapidly establishing the intravenous transfusion depends on both a health care professional's first-stick success technique, and the patient's vein thickness and its position.

The traditional intravenous infusion technique is using a rigid (metal) needle to penetrate the vessel for infusing liquid medicine. After infusion, the needle has to be pulled out. In most cases, repeated infusion procedure is needed for treatment. Therefore, patients have to suffer from needle stick for each infusion.

In patients with chronic diseases, longtime infusion is often needed. In these patients, steel needle has to be remained in the patients' vessel for a long time. Sometime the steel needle tip penetrates the vessel wall while the limb is moved. This failure of the infusion can cause bleeding and fluid extravasation that can cause pain and surrounding tissue edema and damage. Thus, the needle must be pulled out and another vessel penetration is not avoidable.

Current technology has used the soft plastic catheter for intravenous infusion (Chinese Patent CN2163653Y, 05/041994). After a soft plastic catheter as a sleeve on the steel needle be used for penetrating the vessel wall, the steel needle will be pulled out, then the catheter will be remained in the vessel for infusion. The catheter will then be connected to the intravenous infusion set. Thus, the soft plastic catheter will not injured and penetrate the vessel wall during infusion as that seen in needle set, the repeated needle stick is avoid.

However, all of infusion catheters have the blunt-cutting edge on its tip. The flat edge is 90° to the long axis catheter wall (as shown in FIG. 3 of Chinese patent CN1468637A). The catheter tip is relatively soft and blunt. It is not so easy to be inserted into the vessel wall as the steel needle tip, since there is a certain resistance when it penetrating through the vessel wall. Sometimes, the edge of the tip will be dilated as "bell" shape, or tear, due to the extra force is used for insertion, the catheter can not be inserted into the vessel, then the catheter must be changed and reinserted.

Additionally, the design of the handle of the catheter-needle currently available is round shape, it is not easy to be fixed on the body surface. This is another disadvantage of the current design.

On another hand, recent advance in the design of infusion catheter has been focused on effectively safeguard healthcare workers from accidental needle stick injuries. In a Chinese patent CN1135122C, published in Jan. 21, 2004 has shown the design of a "multipurpose safety intravenous infusion catheter needle" that consist with a trifurcate connector, an infusion soft needle, a steel needle, and an infusion catheter. The first and second connector on the trifurcate connector is the one the same axial and toward to the needle tip. There is a rubber cap on the end of the second connector. The soft needle catheter is on the first connector. The steel needle body slidably fitted in a sleeve and axially passed in the soft needle. The sleeve is connected with the second connecting section of the trifurcate connector. An infusion catheter is connected with a third connecting section of the trifurcate connector. After the soft needle catheter inserted into the patient's vein with the steel needle, the steel needle will be pulled out from the end of the sleeve, the needle will be kept in the sleeve, this improvement can avoid the needle exposed, which can caused accidental needle-stick injury to the others, then cause infection.

However, this design still has some short-comings:

1) The steel needle has to be pulled out from the soft needle catheter manually, this distance is not so short, so it is not so convenient for the operator;
2) The trifurcate is not so easy to handle. More particularly to patients with obesity, excessive bleeding, dehydrate, etc., the vein is hard to find, it is difficult to find the vein and insert the needle catheter quickly and accurately for the healthcare professional. Thus, it is not only waist the time, and also can cause the unnecessary suffering for the patients.
3) The outside contours of the cross section profile of the trifurcate soft needle catheter is round shaped, it is difficult to be fixed on the patients' body surface, it is also easy to be rotated or moved after it be fixed during the infusion.

SUMMARY OF THE PRESENT INVENTION

An object of the present invention is to provide a safety transfusion catheter adapted for infusing a liquid into the blood vessel of human body, which is capable of satisfying the requirement not only for the long-time indwelling the infusion catheter in the vein, and but also for more than one time penetrating the vessel wall. That is to say, the present invention is convenient for handling during the procedure of penetrating the vessel wall, and fixing on the body surface. As a result, the vessel injury can be minimized, the infusion process can be carried on quickly and easily. The patient's unnecessary suffering will be reduced.

The technical scheme of the present invention is to provide safety infusion catheter, which comprises a flexible retention tube coating on a metal guiding needle having a wedge-shaped needle tip, and connected with a needle handle, wherein an angle between an end portion of the flexible retention tube and a longitudinal axis or a longitudinal tube wall thereof is less than 90°, wherein a cross section of the needle handle has an outer contour line of a closed curve formed with a curve intersecting a beeline.

Specially, the end portion of the flexible retention tube is parallel to the wedge-shaped needle tip of the metal guide needle, a tube wall of the end portion of the flexible infusion needle catheter tube has a chamfer angle, the end portion of the flexible infusion needle catheter tube is smoothly connected with two joint portions of an outer wall surface of the flexible infusion needle catheter tube respectively.

The curve is a circular arc curve, elliptical arc curve, drop-shaped curve or a combination of the circular arc curve, elliptical arc curve, and drop-shaped curve.

Furthermore, the outer contour line of the cross section of the needle handle is semicircular, semielliptical, semi drop-shaped, approximately semicircular, approximately semielliptical, approximately semi drop-shaped, or their combinations.

The needle handle comprises two hinge members, each of which comprises a buckle at an opening thereof respectively, wherein each of the two hinge members has a groove at an inner side thereof in such a manner that when the two hinge members are engaged with each other, the grooves of the two hinge members form a hollow cavity for fittedly and shapedly receiving the needle handle therein so that the needle handle is detachably inserted into the two hinge members.

A plurality of anti-skid threads are provided on an outer surface of the needle handle.

A safety transfusion needle catheter comprises a flexible retention tube coated on a metal guiding needle, a transfusion connecting tube communicating with the flexible retention tube, and a rubber plug at an end of the flexible retention tube, wherein a back end of the metal guiding needle is slidably engaged and coaxially aligned with a hollow sleeve, wherein the transfusion connecting tube and the flexible retention tube form a T-shaped or an oblique Y-shaped structure, wherein a safety protection sleeve is provided in a front end of a sleeve cap, a length of which is shorter than that of the metal guiding needle, wherein a spring is provided between an end hub of the metal guiding needle and the front end of the hollow sleeve cap, wherein a seesaw type stop block is provided in the hollow sleeve, wherein a reset button is provided on a portion of the hollow sleeve cap having the seesaw type stop block.

The metal guiding needle is slidably provided in the hollow protection sleeve, wherein the spring is coated on the metal guiding needle, wherein the seesaw type stop blocker is provided at an end of the metal guiding needle that allows the needle to be completely out of the sleeve into to the flexible catheter tube, wherein the protection sleeve and the metal needle are inserted through the rubber plug into the flexible catheter tube at an operating position.

A wing-shaped or a butterfly-shaped handle accessory is provided at a conjunction of the infusion connection tube and the flexible infusion tube, wherein one side of the handle accessory is a plane, wherein a plurality of anti-skid threads are provided on an outer surface of at least one side of the needle handle accessory.

The handle accessory is a two pieces-hinge structure buckled together, which is detachably provided on the conjunction of the infusion connection tube and the flexible infusion tube.

These and other objectives, features, and advantages of the present invention will become apparent from the following detailed description, the accompanying drawings, and the appended claims.

DETAILED DESCRIPTION OF THE PREFERRED EMBODIMENT

Figure 1:
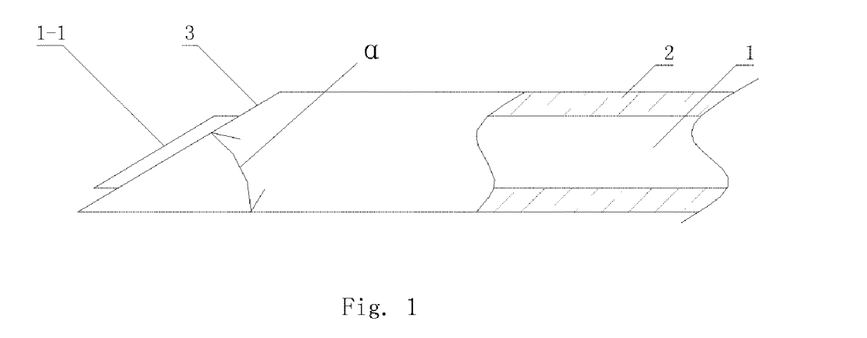
FIG. 1 shows a schematic drawing of the end portion of the flexible infusion catheter of the present invention.

In FIG. 1, the present invention comprises a metal guide needle 1 having a wedge-shaped needle tip portion 1-1, and a flexible infusion needle catheter tube 2 coated on the metal guide needle 1. An angel between an end portion of the flexible infusion needle catheter tube 3 and a longitudinal axis or longitudinal tube wall thereof is less than 90°.

Furthermore, the end portion of the flexible infusion needle catheter tube 3 is parallel to the wedge-shaped metal needle tip portion 1-1 of the metal guide needle 1.

A longitudinal section of the end portion of the flexible infusion needle catheter tube 3 is non-planar, wedge-shaped so that when the flexible infusion catheter penetrates the vessel and advances into the vessel after penetration, the resistance is reduced.

Figure 2:
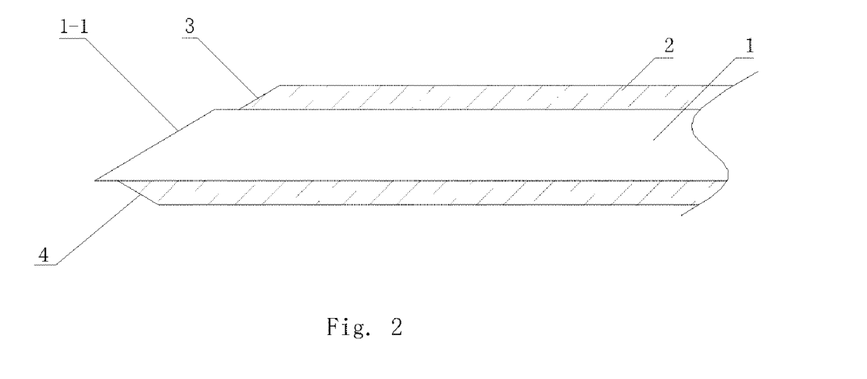
FIG. 2 is the diagram of a preferred embodiment of FIG. 1.

Referring to FIG. 2, to further reduce the resistance of the flexible infusion catheter during penetration and insertion, a tube wall of the end portion of the flexible infusion needle catheter tube 3 has a chamfer angle 4.

Remaining is the same as described above.

Figure 3:
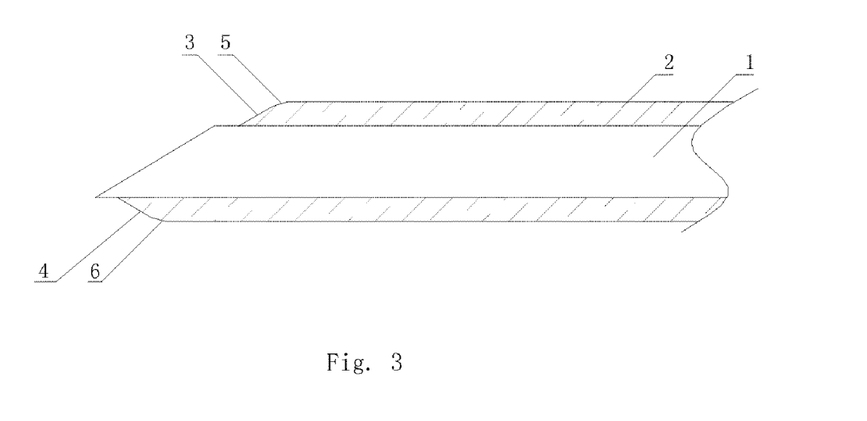
FIG. 3 is the diagram of another embodiment of FIG. 1.

In FIG. 3, the end portion of the flexible infusion needle catheter tube 3 is smoothly connected with two joint portions 5, 6 of an outer wall surface of the flexible infusion needle catheter tube 2 respectively.

The above mentioned smooth transition structure could also reduce the resistance of flexible infusion catheter during penetration and insertion, prolong the service life, improve the first-stick success, and it will also minimize the vessel wall injury during penetration and insertion.

Remaining is the same as described above.

Considering simplifying the processing technology, as a simple structure, a non-planner arch-shaped structure can be used at the end portion of the flexible infusion needle catheter tube 3.

Figure 4:
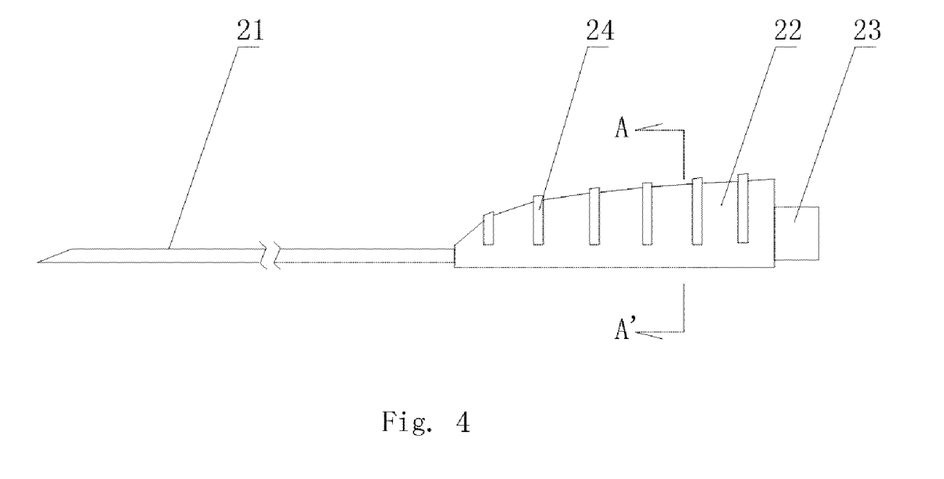
FIG. 4 is the structure diagram of the needle handle of the present invention.

In FIG. 4, the present invention comprises a needle 21 and a needle handle 22 connected with the needle 21. A plurality of anti-skid threads 24 are provided on an outer surface of the needle handle 22. A back end of the needle handle has a connecting opening 23 for the infusion.

Figure 5:
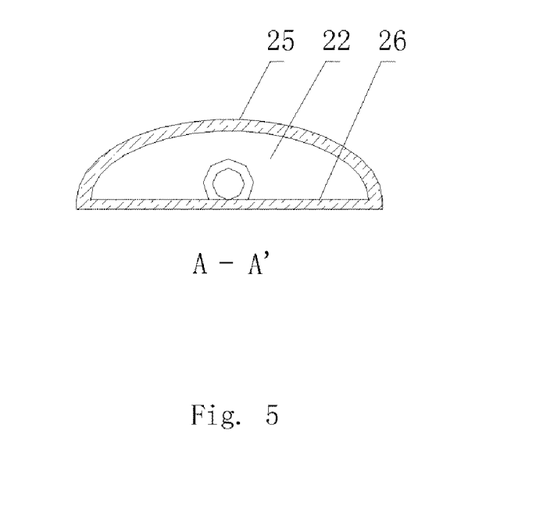
FIG. 5 is the A-A' sectional view of FIG. 4.

In FIG. 5, an outer contour line of the cross section of the needle handle 22 is a closed curve formed with a curve intersecting a beeline. The curve could be a circular arc curve, elliptical arc curve, drop-shaped curve or their combinations.

In addition, the outer contour line of the cross section of the needle handle 22 could be a semicircular, semielliptical, semi drop-shaped, approximately semicircular, approximately semielliptical, approximately semi drop-shaped, or their combinations.

As it shown in FIG. 5, the outer contour line of the cross section of the needle handle could be a closed curve formed with a circular arc line 5 intersecting a beeline 6.

Since one side of the needle handle is a plane, this needle handle is easy to be fixed on the patient's body surface.

Remaining is the same as described above in FIG. 4.

Figure 6:
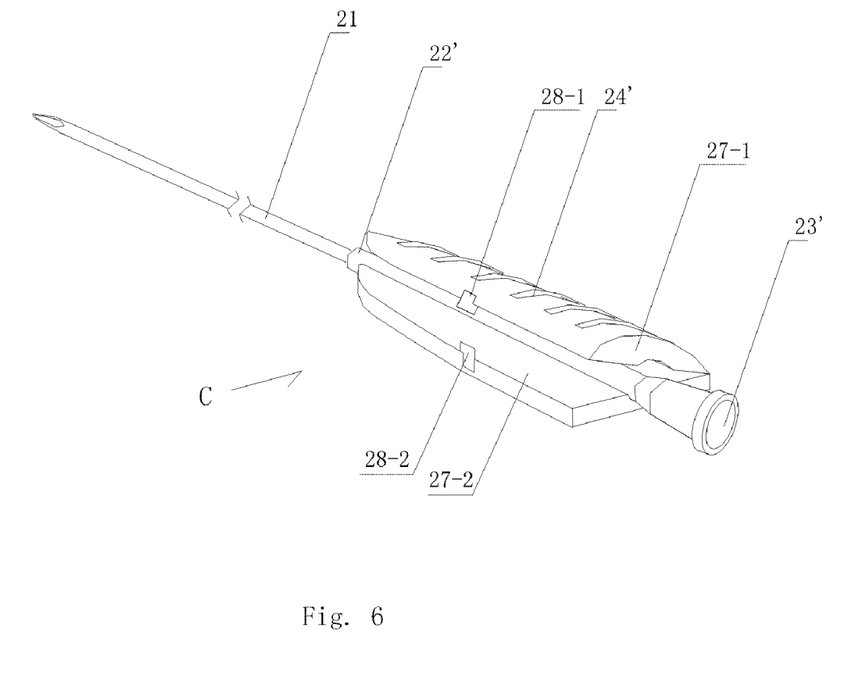
FIG. 6 is another structure diagram of the needle handle of the present invention.

In FIG. 6, the present invention further comprises a needle handle accessory. This handle accessory comprises two hinge members 27-1, 27-2, each of which comprises a buckle 28-1, 28-2 at an opening thereof respectively. Each of the two hinge members 27-1, 27-2 has a groove at an inner side thereof in such a manner that when the two hinge members 27-1, 27-2 are engaged with each other, the grooves of the two hinge members 27-1, 27-2 form a hollow cavity for fittedly and shapedly receiving the needle handle therein, wherein the needle handle is detachably inserted into the two hinge members 27-1, 27-2.

The outer contour line of the cross section of the needle handle accessory is similar as what is shown in FIG. 5.

A plurality of anti-skid threads 24' are provided on an outer surface of the needle handle accessory as well.

Figure 7:
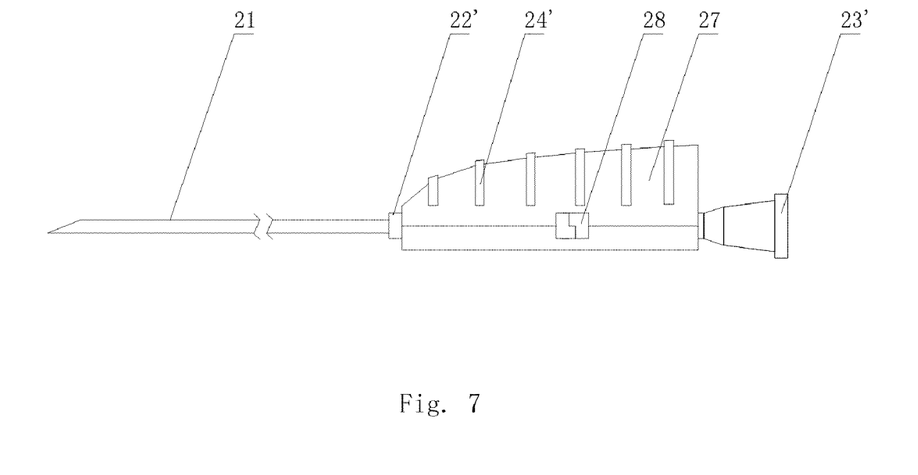
FIG. 7 is a C section view of FIG. 6.

In FIG. 7, when the two hinge members 27-1, 27-2 are engaged with each other, the grooves of the two hinge members 27-1, 27-2 form a hollow cavity at a closed position for fittedly and shapedly receiving the needle handle therein, wherein the needle handle is detachably inserted into the two hinge members 27-1, 27-2.

Remaining is the same as described above in FIG. 6.

Figure 8:
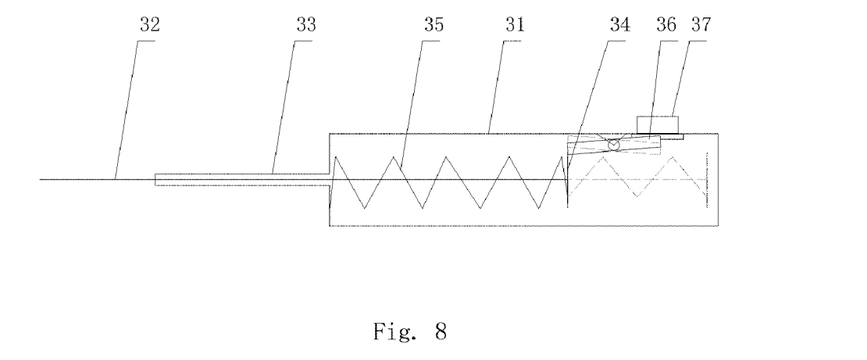
FIG. 8 is the structure diagram of the metal guiding needle component of the present invention.

Referring to FIG. 8, a safety protection sleeve 33 is provided in a front end of a sleeve cap 31, a length of which is shorter than that of the metal guiding needle 32. A spring is provided between an end hub 34 of the metal guiding needle 32 and the front end of the hollow sleeve cap 31. A seesaw type stop block 36 is provided in the hollow sleeve 31. A reset button 37 is provided on the portion of the hollow sleeve cap 31 having the seesaw type stop block 36.

The metal guiding needle is slidably provided in the protecting sleeve 33 and the hollow sleeve cap 31. The spring is provided on the metal guiding needle. A seesaw type stop block is provided behind the back end while the metal guiding needle is completely out of the hollow sleeve cap.

While the reset button is pressed, the seesaw type stop block is disconnected with the end hub, the end hub moves backward owing to the spring to bring the metal guiding needle to rapidly retract. This design is able to achieve the goal for single-hand handle, and quick and easy operation".

Since the protection sleeve is provided, the metal guiding needle only needs travel from the front end of the flexible infusion catheter to the front end of the safety protection sleeve, and achieve the goal of the safety, although the moving distance for the metal guiding needle is greatly decreased, the hollow sleeve cap is much shorter and thinner.

Figure 9:
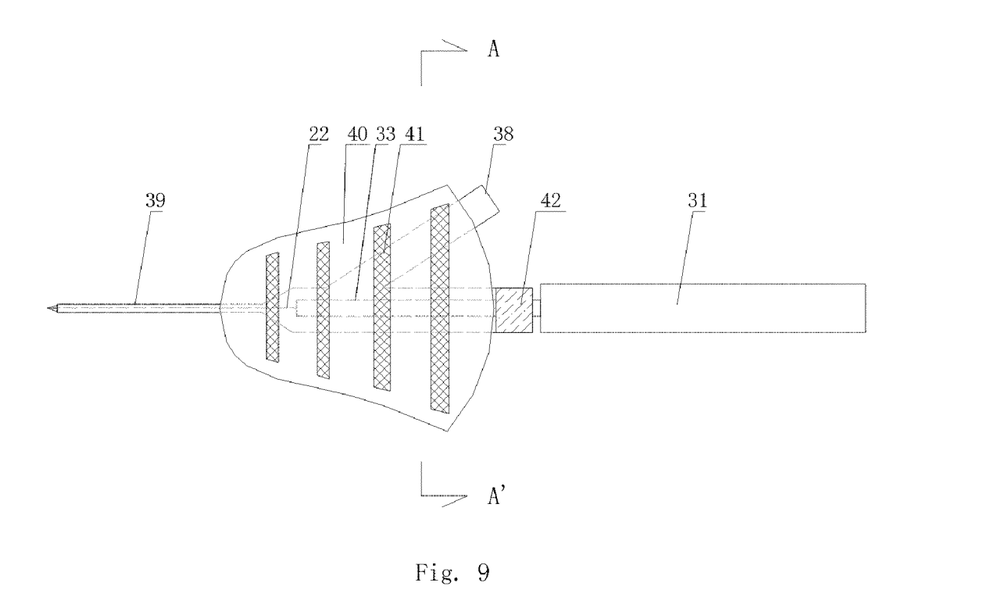
FIG. 9 is the structure diagram of the auxiliary needle handle.

As shown in FIG. 9, a wing-shaped or a butterfly-shaped handle accessory 40 is provided at the conjunction of the infusion catheter tube 38 and the flexible transfusion needle catheter tube 39. A plurality of anti-skid threads 41 are provided on the surface of at least one side of the handle accessory.

Furthermore, the handle accessory is a two-pieces-hinge structure that can be buckled up, and can be provided on the conjunction of the infusion tube and the flexible infusion needle catheter tube. Since this handle structure is well understood by the technical professional in this field, the figure is not shown.

Providing the protection sleeve reduced the length of the safety hollow sleeve, and reduces the required force of spring while retracting the metal guiding needle into the safety hollow sleeve. On another hand, this design also increased its contact area with the rubber plug that prevents the metal guiding needle cutting the plug, reduces the chance for excluding open or enlarge the needle hole on the plug, resulting fluid leaking from the needle hole, keeps the sealing effect of the plug. This design can also reduce the required thickness of the rubber plug, thus further reduces the required force for the spring, increase the feasibility.

Figure 10:
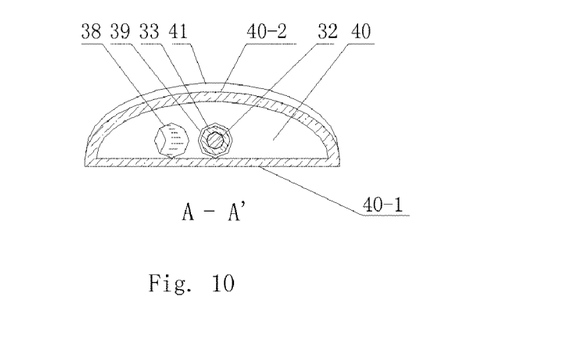
FIG. 10 is the A-A' sectional view of FIG. 9.

In FIG. 10, one side 40-1 of the handle accessory 40 is a plane, a plurality of anti-skid threads 41 are provided on the surface of another side 40-2 so as to easily handle and operate.

As a model and expansion, a design for the detachable infusion needle catheter is show as following:

Providing a back block on the flexible infusion needle catheter, on the back-end of the back block inserts a seepage-preventing rubber plug. The set of the metal guiding needle with safety protective sleeve and its components are provided in the back block of the flexible needle catheter. A needle can be inserted into the seepage-preventing rubber plug is provided in the front end of the infusion catheter. First inserting the flexible infusion needle catheter with the metal guiding needle into the vessel, after extruding the metal guiding needle, inserts the needle on the infusion tube into the back end of the back block of the flexible infusion catheter, for fluid infusion. This can also achieve the goal and effect of this invention. The schematic illustrations of this application have been shown in FIGS. 11 and 12.

In this embodiment of the invention, the illustrations in FIGS. 1-10 are also applicable, for making the figures concise, they have not been shown, but this should not be used for limiting the present invention.

Figure 11:
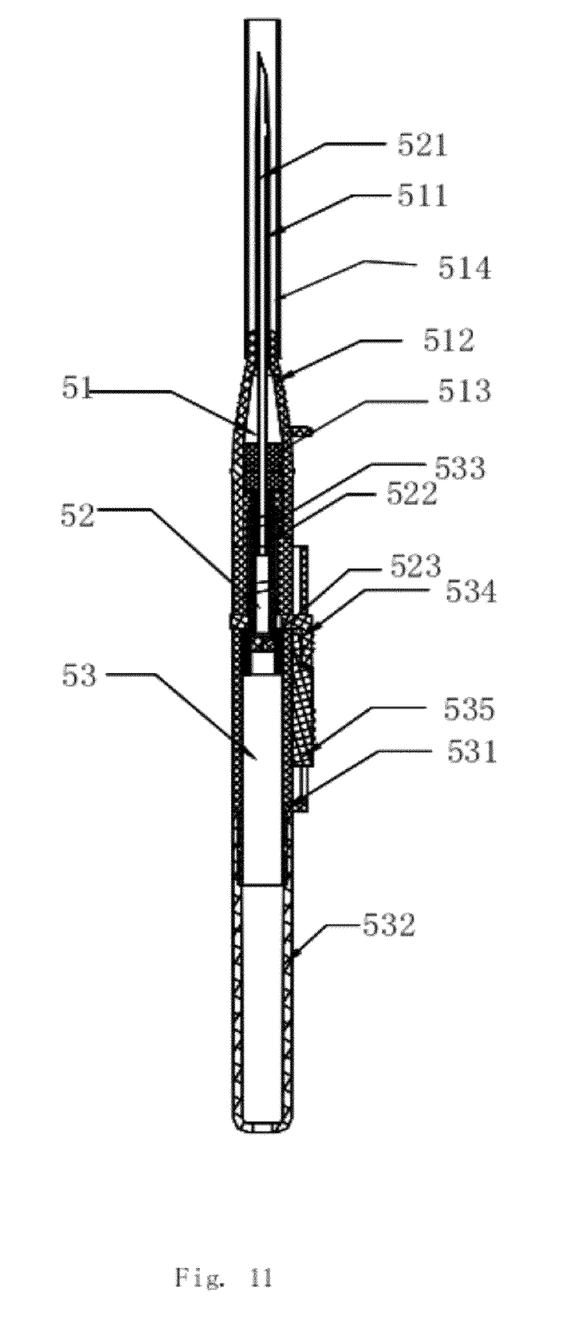
FIG. 11 is structure diagram of the second embodiment of the metal guiding needle component of the present invention.

FIG. 11 combined with FIG. 8 illustrates the flexible infusion catheter needle, the block of flexible tube, rubber plug, and protective sleeve. The blood seepage preventing flexible needle catheter 51 in consist with flexible infusion needle catheter 551, flexible tube block 512, rubber plug 513, and protective sleeve 514.

In the front end of flexible infusion catheter provides a conical narrow part, its back end is connected with the opening of the small tube in the front end of the flexible catheter block. The inner opening of the flexible catheter block connected with the inner opening of the flexible infusion needle catheter tube through the conical hole. The rubber plug is fixed in the middle of the cylindrical hole.

The metal guiding needle components 53 consists of a protective sleeve 511, safety hollow sleeve cap 532, spring 533, seesaw typed stop block button 533, rest-locking button 535. The metal guiding needle protrudes out of the front end of the protective sleeve. A horizontal slot and the vertical chute slot are provided on the front part of the protective sleeve. The positioning plate of the seesaw typed stop block button is inserted into the slot, and embedded into the slot of the needle block, thus, the metal guiding needle is fixed in front end of the protective sleeve, and the spring is compressed before using. The reset-lock key is fitted in the chute slot, the locking plate is embedded in the bottom of the seesaw typed stop block button to prevent it be the accidently pressed before the flexible infusion needle catheter is successfully inserted into the vessel. The safety hollow sleeve cap is connected with the protective sleeve as a whole by a flip block.

When opening the reset-locking key and pressing the seesaw typed stop block button, the whole body of the metal guiding needle is retracted from the flexible infusion needle catheter and completely back into the protective sleeve and the safety hollow sleeve cap.

Remaining are the same as that in FIG. 8.

Figure 12:
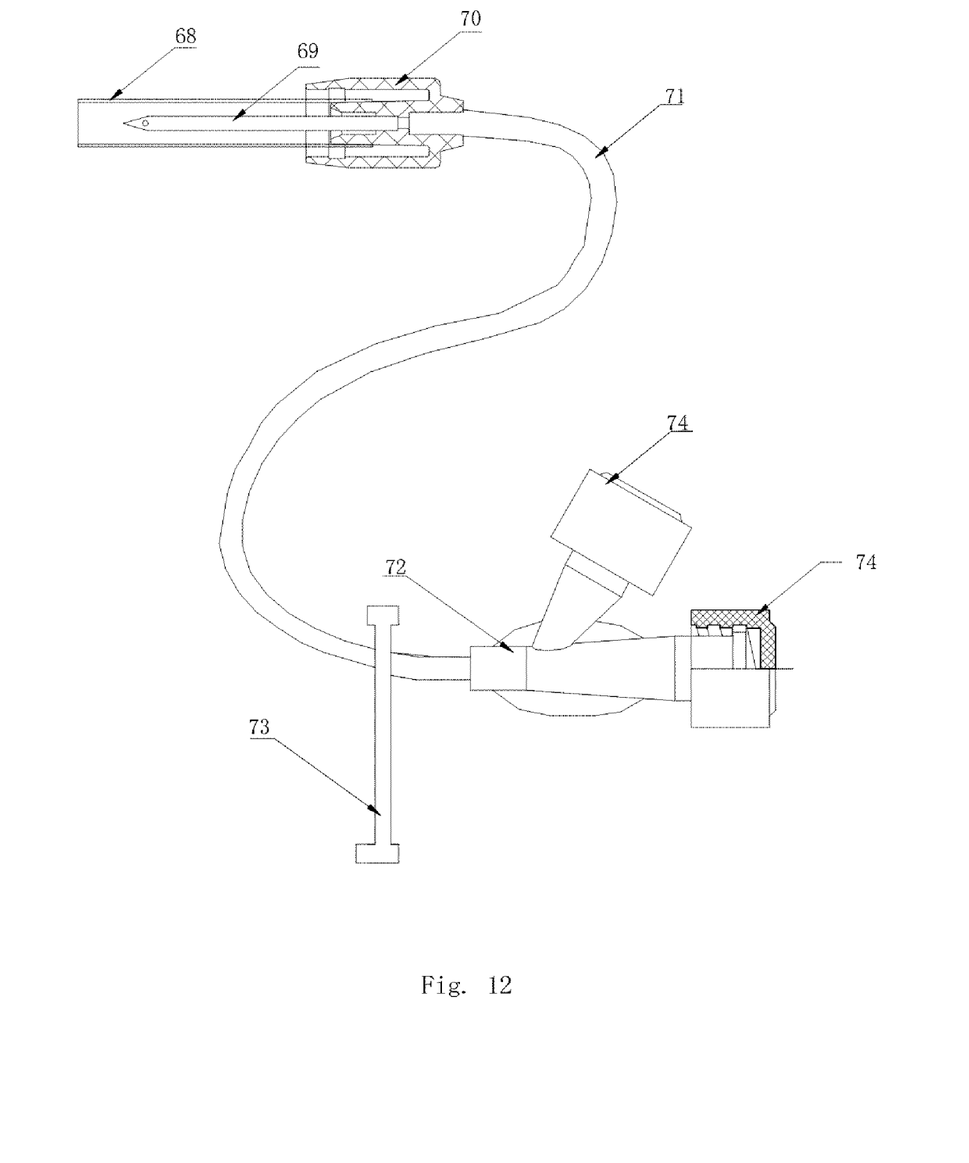
FIG. 12 is s perspective assembled view of the plug-in connection between the infusion catheter and the conjunction of the flexible infusion catheter, needle and the distal end of the infusion catheter.

While using the design shown in FIG. 11, in order to make connection between the blood seepage preventing flexible infusion needle catheter and the infusion tube, the plug-in type connection tube could be used as shown in FIG. 12, that consist with flexible infusion needle catheter tube 69, needle tube block 70, catheter 71, tube clip 73, Y shaped connecter or 3-way stopcock 72 and block cap 74.

There is an oblique cone shaped needle tip in the front end of the insertion needle, its back end connected with the front end of the needle block. The back end of the needle block is connected with the front end of the infusion catheter. Another end of the catheter connected with the Y shaped connector body.

Other two end of the connecter body provide cone Ruhr lock connector. The block cap can be used for blocking the flow before using or stop using. A tube clip is provided for additional control of the flow for convenience. The over long protective needle sleeve covers the needle that is able to fit on the outside of the connector of the flexible catheter blocker.

While using the designed plug-in type infusion tube connector shown in FIG. 12 with the blood seepage preventing flexible infusion needle catheter shown in FIG. 11, first, the blood seepage preventing flexible infusion needle catheter with the metal guiding needle components are used for making the penetration into the vessel, then extrude the metal guiding needle and take out the needle components. After inserting the plug-in connector with infusion tube into the protective sleeve and the rubber plug on the blood seepage preventing flexible infusion needle catheter, then infusion can be initiated. Alternatively, the plug-in type infusion tube connector system shown in FIG. 12 can also be connected to the infusion connector through direct conjunction on the T or Y shaped safety flexible infusion needle catheter system shown in FIGS. 10, and 11.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

Applications

The present invention has following advantages: the flexible retention tube is provided with a non-planar, wedge-shaped cutting edge that is parallel with the metal guiding needle cutting edge, and the less than 90° chamfer and polishing is made on the cutting edge of the tube wall. These improvements will reduce the resistance of the flexible infusion catheter during penetrating and advancing in the vessel, reduces the vessel injury and greatly improve the chance of first-stick success. One side of the needle handle is planner, that will helpful for fixing it on the patient's body surface. Providing the seesaw type stop block, reset-locking button, and the design for shorter spring moving distance, allows the metal needle fast retracting into the safety sleeve. With additional improvements made in the design for the preventing blood seepage eliminates the possible blood contamination, this invention provides total safety working condition, and feasibility for assembly and production. This invention has avoided the many disadvantage of the current design, fulfilled the requirements for long time infusion, and repeated penetration. This design has reached the goal for easy operating, and at the same time minimizing vessel injury.

What is claimed is:

1. A safety transfusion needle catheter, comprising:
a metal guiding needle having a wedge-shaped needle tip,
a flexible retention tube encircling said metal guiding needle, wherein an angle between an end surface of a first end of said flexible retention tube and a longitudinal tube wall of said flexible retention tube is less than 90-degree; and
a needle handle connected with a second end of said flexible retention tube, wherein in a cross section of said needle handle, an outer contour line thereof is a closed curve formed with a curve intersecting a beeline,
wherein, a first end surface of said first end of said flexible retention tube at one side of said metal guiding needle is parallel to a wedge surface of said wedge-shaped needle tip, an angle between a second end surface of said first end of said flexible retention tube at another side of said metal guiding needle and said longitudinal tube wall of said flexible retention tube is more than 90-degree forming a chamfer angle at said another side of said metal guiding needle, said first end surface and said second end surface of said first end of said flexible retention tube smoothly extend to two longitudinal tube walls of said flexible retention tube, respectively for forming a smooth curve connection between said end surface and said longitudinal tube wall of said flexible retention tube.

2. The safety transfusion needle catheter, as recited in claim 1, wherein said curve is selected from the group consisting of a circular arc curve, an elliptical arc curve and a drop-shaped curve.

3. The safety transfusion needle catheter, as recited in claim 1, wherein said outer contour line of said needle handle is selected from the group consisting of semicircle, semiellipse, semi drop-shape, approximately semicircle, approximately semiellipse, and approximately semi drop-shape.

4. The safety transfusion needle catheter, as recited in claim 1, wherein said needle handle comprises two handle members, each of which comprises a buckle at a side edge thereof engaged with each other and has a groove at an inner wall thereof in such a manner that when said two handle members are engaged with each other, said grooves of said two handle members form a hollow cavity for fittedly and shapedly receiving said flexible retention tube therein so that said flexible retention tube is detachably inserted into said two handle members.

5. The safety transfusion needle catheter, as recited in claim 1, wherein a plurality of anti-skid threads are provided on an outer surface of said needle handle.

6. A safety transfusion needle catheter, comprising:
a hollow sleeve housing,
a safety protection sleeve disposed at a front end of said hollow sleeve housing,
a rubber plug penetrated by said safety protection sleeve and disposed at an end of said safety protection sleeve close to said hollow sleeve housing,
a flexible retention tube disposed at a front end of said safety protection sleeve,
a transfusion connecting tube disposed at a side of said safety protection sleeve and communicating with said flexible retention tube,
a metal guiding needle, having a needle hub at an end thereof and within said hollow sleeve housing, a first portion of said metal guiding needle slidably penetrating through said safety protection sleeve and said rubber plug and disposed within said hollow sleeve housing, a second portion of said metal guiding needle encircled with said flexible retention tube,
a spring disposed within said hollow sleeve housing, between an end surface of said hollow sleeve housing and said needle hub of said metal guiding needle, and sleeved said metal guiding needle,
a seesaw type stop block disposed within said hollow sleeve housing and at a position behind said needle hub of said metal guiding needle when the metal guiding needle is entirely out of said hollow sleeve housing for blocking said needle hub, a reset button disposed at a side of said hollow sleeve housing corresponding to said seesaw type stop block, such that while pressing said reset button, said needle hub of said metal guiding needle is detached from said seesaw type stop block and moves backwardly under an effect of said spring, so that said metal guiding needle is quickly retracted, wherein said transfusion connecting tube and said flexible retention tube form a T-shaped or an oblique Y-shaped structure, wherein a length of said safety protection sleeve is smaller than that of said metal guiding needle.

7. The safety transfusion needle catheter, as recited in claim 6, further comprising a wing-shaped or a butterfly-shaped handle accessory provided at a conjunction of said transfusion connecting tube and said flexible infusion tube, wherein one side face of said handle accessory is a plane, wherein a plurality of anti-skid threads are provided on an outer surface of at least one side face of said needle handle accessory.

8. The safety transfusion needle catheter, as recited in claim 7, wherein said handle accessory is a two pieces-hinge structure buckled together, which is detachably provided on said conjunction of said infusion connection tube and said flexible infusion tube.

9. The safety transfusion needle catheter, as recited in claim 6, wherein said metal guiding needle has a wedge-shaped needle tip, wherein an angle between an end surface of a first end of said flexible retention tube and a longitudinal tube wall of said flexible retention tube is less than 90-degree.

10. The safety transfusion needle catheter, as recited in claim 7, wherein said metal guiding needle has a wedge-shaped needle tip, wherein an angle between an end surface of a first end of said flexible retention tube and a longitudinal tube wall of said flexible retention tube is less than 90-degree.

11. The safety transfusion needle catheter, as recited in claim 8, wherein said metal guiding needle has a wedge-shaped needle tip, wherein an angle between an end surface of a first end of said flexible retention tube and a longitudinal tube wall of said flexible retention tube is less than 90-degree.

12. The safety transfusion needle catheter, as recited in claim 9, wherein in an axially sectional view of said safety transfusion needle catheter, a first end surface of said first end of said flexible retention tube at one side of said metal guiding needle is parallel to a wedge surface of said wedge-shaped needle tip, an angle between a second end surface of said first end of said flexible retention tube at another side of said metal guiding needle and said longitudinal tube wall of said flexible retention tube is more than 90-degree forming a chamfer angle at said another side of said metal guiding needle, said first end surface and said second end surface of said first end of said flexible retention tube smoothly extend to two longitudinal tube walls of said flexible retention tube, respectively for forming a smooth curve connection between said end surface and said longitudinal tube wall of said flexible retention tube.

13. The safety transfusion needle catheter, as recited in claim 10, wherein in an axially sectional view of said safety transfusion needle catheter, a first end surface of said first end of said flexible retention tube at one side of said metal guiding needle is parallel to a wedge surface of said wedge-shaped needle tip, an angle between a second end surface of said first end of said flexible retention tube at another side of said metal guiding needle and said longitudinal tube wall of said flexible retention tube is more than 90-degree forming a chamfer angle at said another side of said metal guiding needle, said first end surface and said second end surface of said first end of said flexible retention tube smoothly extend to two longitudinal tube walls of said flexible retention tube, respectively for forming a smooth curve connection between said end surface and said longitudinal tube wall of said flexible retention tube.

14. The safety transfusion needle catheter, as recited in claim 11, wherein in an axially sectional view of said safety transfusion needle catheter, a first end surface of said first end of said flexible retention tube at one side of said metal guiding needle is parallel to a wedge surface of said wedge-shaped needle tip, an angle between a second end surface of said first end of said flexible retention tube at another side of said metal guiding needle and said longitudinal tube wall of said flexible retention tube is more than 90-degree forming a chamfer angle at said another side of said metal guiding needle, said first end surface and said second end surface of said first end of said flexible retention tube smoothly extend to two longitudinal tube walls of said flexible retention tube, respectively for forming a smooth curve connection between said end surface and said longitudinal tube wall of said flexible retention tube.

* * * * *